(12) United States Patent
Selker

(10) Patent No.: US 7,580,128 B2
(45) Date of Patent: Aug. 25, 2009

(54) LINEAR OPTICAL LOSS PROBE

(75) Inventor: Mark Selker, Los Altos Hills, CA (US)

(73) Assignee: Finesse Solutions, LLC., San Jose, CA (US)

( * ) Notice: Subject to any disclaimer, the term of this patent is extended or adjusted under 35 U.S.C. 154(b) by 259 days.

(21) Appl. No.: 11/893,033

(22) Filed: Aug. 14, 2007

(65) Prior Publication Data
US 2009/0027670 A1 Jan. 29, 2009

(51) Int. Cl.
G01N 21/00 (2006.01)
(52) U.S. Cl. ........................ 356/338; 356/336
(58) Field of Classification Search ................... 356/338
See application file for complete search history.

(56) References Cited

U.S. PATENT DOCUMENTS 6,266,137 B1 * 7/2001 Morinaga ................ 356/237.1
6,842,243 B2 * 1/2005 Tokhtuev et al. ............ 356/338
2003/0117623 A1 * 6/2003 Tokhtuev et al. ............ 356/338
2008/0114550 A1 * 5/2008 Paldus et al. .................. 702/19

* cited by examiner

Primary Examiner—Roy Punnoose
(74) Attorney, Agent, or Firm—Herbert Burkard

(57) ABSTRACT

An optical loss probe utilized as a bioreactor process monitor manifesting a substantially linear response in optical loss vs. concentration of scatterers present in an aqueous medium in the range of between about 0 AU and about 4.0 AU, said probe comprising:
i) a light source,
ii) an optical detector, and
iii) an optical gap between said light source and said optical detector, said optical detector having a receiving aperture configured such that the solid angle of acceptance of the light passing through said optical gap and impinging on said optical detector is less than $\pi/50$ radians.

22 Claims, 12 Drawing Sheets

Prior Art

Figure 1 (time vs. optical loss graph)

LINEAR OPTICAL LOSS PROBE

RELATED APPLICATIONS

This application claims priority from copending, commonly assigned application Ser. No. 11/591,360, filed Nov. 1, 2006, and is related to commonly assigned application Ser. No. 11/702,861, filed Nov. 10, 2006.

FIELD OF THE INVENTION

This invention relates to an improved instrument and method for the monitoring of biological reactions such as fermentation.

BACKGROUND OF THE INVENTION

A bioreactor can be defined as a system in which a biological conversion is effected. This definition can apply to any conversion involving enzymes, micro-organisms, or animal, insect or plant cells. Artworkers sometimes distinguish between a bioreactor and a fermentor since in the strictest sense a fermentor is a system that provides an anaerobic process for producing alcohol from sugar. The dichotomy in nomenclature is most often used to distinguish between animal and bacterial cell culture despite the fact that a bioreactor and a fermentor are generally similar in design. However, we will use the word bioreactor in a generic sense to refer to any type of container (usually made of glass, metal or polymer) in which organisms including microbes, animal, insect or plant cells and bacteria (all being hereinafter referred to generally as "cells") are cultivated in a controlled manner. Therefore, unless otherwise indicated, the term bioreactor will be considered as including a fermentor.

The goal of an effective bioreactor is to contain, control, and positively influence a particular desired biological reaction. One desired biological reaction considered here is the growth of unicellular microorganisms. The most popular method for accomplishing this is a batch cultivation system. See, for example, James Lee, *Biochemical Engineering*, Washington State University, e-book, 2002. For simplicity and clarity we will describe in detail here a batch process, although the analytical apparatus and methods described and claimed herein apply also to continuous growth processes (e.g.: perfusion). In a batch method, the microorganisms are inoculated into the culture medium and the growth cycle then commences. This growth cycle comprises the following phases:

1. Lag phase: A period of time during which the cells have not yet commenced growth
2. Accelerated growth phase: The period during which the number of cells increases and the cell division rate reaches a maximum.
3. Exponential growth phase: The period during which the number of cells increases exponentially as the cells divide. The growth rate (cell concentration) is increasing during this phase, although the cell division rate is substantially constant and at its maximum.
4. Decelerated growth phase: After the growth rate has reached a maximum it is followed by a deceleration in both the growth rate and cell division rate.
5. Stationary phase: The cell population reaches a maximum value and thereafter does not significantly increase.
6. Death phase: After nutrients available to the cells are depleted and/or the bioreactor environment becomes too hostile, cells will start to die and the number of viable cells will decrease.

These stages are graphically illustrated in FIG. 1 which shows the change in measured cell density (concentration) vs. time for a typical bioprocess with each of the six phases indicated.

In order to optimize the growth process, it is beneficial to monitor the growth process by observing the change in cell density during each of the six phases described above. In particular, it is desirable to achieve maximum yield by harvesting the cells at stage 5, or as close thereto as possible, i.e., when the maximum number of viable cells is present in the bioreactor growth medium. In the past, the monitoring of cell density was done off-line. Off-line here means not being in real time, and is conventionally done by taking a sample out of the bioreactor for examination. The examination is often accomplished either by drying and then weighing the dried sample or by diluting the drawn sample and placing the diluted sample in a spectrophotometer. The dry cell weight is generally considered the most accurate method, but it often takes 7-10 days to obtain the results. This time lag renders it impossible to effect any change in reaction conditions in the run under study; and obviously control loops can not be implemented. Another prior art, off-line method using a spectrophotometer is often called an optical density measurement. This optical method is common but is also not a true real time measurement and has accuracy issues associated with its implementation, specifically the need to highly dilute the sample removed from the bioreactor so that its optical loss is within the dynamic operating range of the spectrophotometer.

Due to the time, effort, and lack of availability of real time information with the aforementioned off-line cell density measurement methods, many attempts to automate this measurement and make it real time have been made. Recently, so called turbidity probes have been employed to give a measurement which can be related to the cell density in a bioreactor. A picture of a typical prior art turbidity probe used for this application is shown schematically in FIG. 2. In this device a light source 2 is used to illuminate a gap 4 in which the cell containing, bioreactor liquid under study is located. The light traverses the gap, and that portion of the light that is not scattered or absorbed by the liquid is incident upon the detector 5 and gives a signal. It is desirable that a strong linear correlation exist between the cell concentration in the medium in the gap, and the signal arriving at the detector. Electronics and firmware are sometimes configured such that a baseline reading in a neutral fluid (e.g.: de-ionized water) is used for comparison. However, the resulting measurements are often not as linear or strongly correlated to cell density as is necessary. The reasons for this discrepancy and a solution in accordance with the present invention are discussed below.

Many of the turbidity meters currently used in the biotech area have their heritage in turbidity measurements for wastewater characterization. The commonly used definition of turbidity also has its origin in the wastewater industry and is, "Turbidity, an expression of the optical properties of a liquid that causes light rays to be scattered and absorbed rather than transmitted in straight lines through a sample" [see ASTM Standard Test Method for Turbidity in Water, D 1889-00, ASTM International, 2002)] In general, this is not a specific enough description of the physical phenomenon to permit a concise mathematical definition. Without a precise mathematical definition, it is difficult to define and construct a precise and repeatable measuring method or instrument. This problem is one reason why the United States EPA has apparently experienced difficulty in getting the various vendors of turbidity meters to agree with each other on a measurement standard. Unfortunately, all of the turbidity meters currently being used to give measurements proportional to cell density are limited in at least one of several essential ways. The limitations frequently stem from the use of incoherent, broad bandwidth light sources such as lamps and LEDs, and/or large optical beams and large field of view detectors. These limitations manifest themselves in the way the probe respond to a bioreactor medium in which significant scattering occurs and can frequently therefore lead to ambiguous results. An additional ambiguity results from the fact that the size and refractive index of the bioparticle (cell) will frequently change during the course of the cell growth process.

Also, part of this ambiguity is due to the fact that scattering phenomena are inherently difficult to describe precisely [see Akira Ishimaru, Wave Propagation and Scattering in Random Media, IEEE Press 1997]. For example, scattering does not strictly follow Beer's law, which holds rigorously only for absorbing solutions and even then only up to the point where the concentration of the solute becomes sufficiently high that electrostatic interactions occur which actually change the solute's absorptive properties. In a scattering medium, Beer's law will generally only hold up to around 1 AU of loss where loss in AU is defined as:

$$\text{Loss} = \text{Absorbance} \equiv \text{Log}_{10}\left[\frac{I_t}{I_0}\right] AU \quad \text{Eq. 1}$$

where $I_t/I_0$ is the ratio of the transmitted intensity to the initial intensity. It should be noted that the use of the units AU or absorption units is somewhat of a misnomer for scattering systems. Although the language and machinery of Beer's law is based on absorptive loss, turbidity probes for cell density measurement nevertheless generally give their results in AU; although occasionally turbidity units NTU (nephelometric turbidity units) or JTU (Jackson turbidity units) are employed. It should also be noted that off-line cell density measurement using a spectrophotometer owes its accuracy problems in part to the fact that the samples drawn from a bioreactor need to be significantly diluted in order to allow the spectrophotometer to operate in a regime where it sees less than 1 AU of loss.

Herein when we refer to Beer's law, we refer specifically to the exponential decay of light intensity as a function of distance or with the concentration of a target analyte dispersed in a medium. This can be expressed mathematically as:

$$I(x)/I(0) = I_t/I_0 = e^{-\xi x} \quad \text{Eq. 2}$$

Here $\xi$ is the combined loss coefficient due to both scattering and absorption, x is the distance the optical beam has propagated into the sample, and $I_t/I_0$ is the ratio of the transmitted intensity to the initial intensity where $I_t$ represents the intensity transmitted through the medium from the origin to point x, and e is the base constant of the natural logarithm=2.71828183. This type of behavior is shown in FIG. 3 where, for ease of illustration, the exponent has been defined as unity.

Very often the base 10 logarithm of both sides of Equation 1 is used and a linear relationship is thereby established between the incident and transmitted light intensity. This linear relationship, which defines the absorbance A, is shown in Equation 3:

$$A(\lambda, c) = \text{Log}_{10}\left[\frac{I_t}{I_0}\right] = k\xi L \quad \text{Eq. 3}$$

Here k is the base 10 logarithm of e. This linear relationship between absorbance, A, and loss coefficient $\xi$, or distance L in the x direction is a linear representation of Beer's Law. This depiction is sometimes useful because of the inherent simplicity of a straight line. An example is show in FIG. 4 for the measurement of absorbance in AU of Copper Sulfate ($CuSO_4$) at 830 nm over a fixed distance with increasing concentration of $CuSO_4$ It has been noted many times and in many disciplines that Beer's law does not rigorously hold for scattering systems. This is often referred to as the "breakdown" of Beer's law. In fact, Beer's law does not break down, but rather only the assumptions under which it is applied. Generally, Beer's law is employed to describe the absorptive attenuation of an optical signal as a function of distance in the medium or as a function of concentration of the absorbing specie or species in the medium. However, Beer's law can also be used to describe the decay of light transmitted from the light source to a detector across a gap containing an absorbing or absorbing and weakly scattering medium.

If one assumes a perfectly collimated optical beam with a cross-sectional area that is no greater than the area of the detector and a purely absorptive medium between the source and the detector, then the only light that reaches the detector is the light that is not absorbed. However, one normally does not have a perfectly collimated optical beam, and in many existing cell density probes, the spatial extent of the beam exceeds the area of the detector. By recording the signal on the detector when a neutral (minimally absorbing, non-scattering) fluid like de-ionized water is present in the gap, it is possible to consider only the light that is actually hitting (impinging on) the detector. However, in a highly scattering (turbid) medium the situation is different irrespective of whether the beam is perfectly collimated and sized or not. Some portion of the light still makes it directly to the detector, but some light is singly scattered into the detector's field of view, and other light is multiply scattered and thereby also ends up in the detector's field of view. It is this scattering of light into the detector (specifically the light that would otherwise miss the detector in the absence of scattering) which causes deviations from what is predicted by Beer's law. Since most currently existing turbidity meters generally utilize a wide, divergent, incoherent optical beam there are many paths the source light can take into the detector. This is depicted in FIG. 5 in which the numbered components are as follows:

6. The optical source
7. A ray that misses the detector
8. The collimated rays that hit the detector
9. A scattering particle
10. A ray that would have missed the detector if it were not singly scattered into the detector
11. A ray that might have missed the detector but is multiply scattered into the detector
12. The detector
13. A collimated ray that would miss the detector if it were not scattered Standard turbidity meters therefore do not accurately follow Beer's Law, and therefore are unable to provide a linear response in absorbance as a function of scattering density beyond ~1 AU. Many fermentation runs and mammalian cell bioreactor growth runs will result in a medium that has an optical loss significantly exceeding 1 AU. This is often troublesome to the end user in the biotechnology arena who is accustomed to the linear response of other bioreactor analytical devices such as electrochemical pH and dissolved oxygen probes. The resulting nonlinear response of the cell density probe must be separated from the actual growth behavior of the cell specimens under study. Equally significant complications arise from the fact that the dynamic range of existing cell density probe is limited by its saturating response. As shown in FIG. 6, the response of a typical probe as a function of increasing density of scatterers (in this example ~2 micron polystyrene micro-spheres) is that it saturates. At some point the slope of the response will approach zero. However, even before the slope reaches zero, a point will frequently be reached where any noise added to the signal will result in a loss of accurate information.

Additionally, it should be noted that the scattering pattern (behavior) of a particle depends heavily on the ratio of the wavelength ($\lambda$) of the incident light to the circumference of the particle [see H. C. van de Hulst, *Light Scattering by Small Particles*, Dover 1981]. Generally speaking, there exist 3 domains of interest from a scattering perspective:

Rayleigh Regime: $d << \lambda$
Mie Regime: $d \sim \lambda$
Geometrical Optics Regime: $d >> \lambda$ with d being the mean particle diameter. In the Rayleigh regime the scattering resembles dipole scattering, while in the Mie regime the scattering has a characteristic forward scattering behavior. The larger the diameter of the scatterer for a given wavelength of incident light, the more light is forward scattered. In the regime where the size of the particle is more than about two orders of magnitude larger than the optical wavelength, the scattering takes on the behavior of ray optics. Typical scattering patterns for Rayleigh and Mie scattering with various sizes of particles are shown in FIG. 7.

I have found that the preferred optimal illumination wavelength for an optical loss probe in accordance with the present invention will be in the near infrared, preferably between 810 and 850 nm and most preferably about 830 nm. At about 830 nm water has its absorption minimum, which means that this wavelength is optimal for a probe that is to measure the decrease in transmissivity by biological material that is present in an aqueous medium, as is normally used for bioprocesses. Light at other wavelengths where there is absorption by the cells can, in principle, be used, but this adds ambiguity to the measurement. Even if the baseline absorption by the medium is accounted for, the mean free scattering path length will change as a function of scattering density, thereby adding uncertainty. Near the water absorption minimum at a wavelength of around 830 nm and given the size of the biological scatterers of interest (e.g.: mammalian cells, microbes), I have concluded that the scattering will be predominantly in the Mie scattering regime. It is important to remember that the magnitude of light scattered forward, as opposed to backwards or to the side, depends on the ratio of the light wavelength to scatterer diameter. As previously mentioned, the larger the scatterer relative to the wavelength, the larger the percentage of the incident light that is scattered forward. This means that for a given wavelength, the scattering density at which the probe's results will deviate from Beer's law will depend on the size of the scatterer. Given this fact, it is clear that the point at which a probe's loss saturates, or is sensitive to noise affecting the measurement, is a variable and will depend on factors including the size of the scatterer which is being measured. This is generally not a preferred situation, and in order to improve upon measurement accuracy, it is necessary to understand the underlying reasons for this variability. These underlying reasons will now be reviewed.

When determining if an analytical technique and/or instrument is suitable for use in monitoring a bioprocess, although it is instructive as a benchmark it is not essential to measure either the absolute concentration of cells or their precise size. The size range of a given cell line is generally known, although it can change during the course of the cell growth process. What is really important is to be able to determine, on a real time basis whether or not the bioprocess is proceeding in accordance with a known growth pattern. To achieve this the bioprocess engineer will seek to monitor cell density (concentration) vs. time or another parameter proportional to cell density. Many process development laboratories utilize a spectrophotometer and the resulting optical density (OD) measurement as a substitute for, or in addition to, manual or automated cell counting in order to monitor the growth process. The point of the invention described herein is to provide a functionally equivalent measurement, but one which is in-line, in real-time, and which manifests a linear response over a broad range of cell density. Existing spectroscopic measurements are incapable of achieving this result. In order to get a quantitative understanding of the cell growth process the user can correlate the optical loss measurement provided by the present invention with total cell density as measured using an automated cell counter such as those offered by Nova or Innovatis (e.g.: The Nova Flex or Nova 400 series (http://www.novabiomedical.com/biotechnology.html) or the Cedex by Innovatis (http://www.innovatis.com/)) by taking off-line samples and noting the results and time of sample. The user can also take samples and perform a dry cell weight measurement, or perform a manual cell count. The important fact is that these quantitative measurements are taken off-line and correlated to an optical loss measurement taken at-line at the same time in accordance with the present invention. A mathematical mapping between the optical loss measurement and the quantitative measurement used as a process variable can then be created and displayed. The apparatus of the present invention does not (and need not) directly measure a size or number density quantity of the cells in the bioreactor. The scattering based optical loss measured in accordance with the present invention does, however, correlate well to a function of mean scattering particle diameter, mean number density, and mean index of refraction. The technique and apparatus of the present invention permit this comparison with a high degree of accuracy and reliability. In other words, my invention provides a means to accurately monitor the course of a bioprocess and confirm whether or not it is proceeding in accordance with FIG. 1.

The prior art, as exemplified by U.S. Pat. No. 6,219,138, teaches a technique for confirming or determining particle size using a single illumination source (or multiple sources if the particle size is unknown). Although there is some similarity between the apparatus described in this patent and that of the present invention, the measurement objectives and results are certainly different and critical aspects of the apparatus of the present invention are likewise different. For example, the present invention always utilizes a single wavelength illumination source (i.e., not broadband), and does not measure (or need to precisely know) the size of the bioparticle, but rather accurately monitors the scattering loss of the reaction media over time i.e., during the course of the bioprocess. As indicated, it operates on the basis of an assumed maximum particle size which will generally be known with sufficient accuracy based on the particular cell being grown, and thereby permits an accurate monitoring of the status of a bioprocess. Additional differences between the product and process of the present invention and those of the prior art include the specific wavelength being chosen (810-850 nm, especially ~830 nm) to be at a minimum of water absorption, and the use of a phase sensitive detection system.

BRIEF DESCRIPTION OF THE DRAWINGS

FIGS. 1 through 11 are illustrative of various aspects of the background of the invention, while FIGS. 12 through 18 are illustrative of the present invention.

FIG. 1 shows the change in measured cell density vs. time for a typical bioprocess with each of the previously described six bioprocess phases indicated.

FIG. 2 illustrates a typical configuration of a prior art turbidity probe.

FIG. 3 is a graph illustrating the exponential decay of light intensity as a function of distance of a dispersed target analyte in an aqueous media.

FIG. 4 is a graph illustrating absorbance in AU of aqueous $CuSO_4$ at 830 nm over a fixed distance with increasing concentration of $CuSO_4$.

FIG. 5 shows the effect of multiple scattering in the case of a prior art turbidity meter.

FIG. 6 shows that the response of a typical cell density probe as a function of increasing density of scatterers (i.e., ~2 micron polystyrene micro-spheres) is that the probe saturates.

FIG. 7 schematically illustrates Rayleigh and Mie scattering.

FIG. 8 is a graphic representation of the solid angle $d\Omega$.

FIG. 9 is another representation of the solid angle which aids in understanding the derivation of Equation 8.

FIG. 10 is a 2D representation of FIG. 8 as used to calculate the solid angle in Equations 9 and 10.

FIG. 11 shows several different ways which have been used to interpret the field of view of an apertured detector according to the prior art.

FIG. 12d is a probe design similar to FIG. 12a but which utilizes a fiber optic cable to perform both the aperturing and limiting of the numerical aperture FIG. 13 is a block diagram of a preferred embodiment of a cell density probe in accordance with the present invention.

FIGS. 14a and 14b shows the results of scattering tests performed using the probe of FIG. 12a.

FIG. 15 is a "phase" diagram plotted on a logarithmic scale showing the backscatter in the Mie regime as compared to the forward direction scatter and giving the magnitude of the scattering as a function of direction.

FIG. 16 shows a version of the present invention that can be utilized in disposable bioreactors such as bag bioreactors.

FIG. 17 shows a preferred embodiment of the present invention in which the excitation source and the detector are offset in angle.

FIG. 18 shows an apertured, backscatter detection system in accordance with the present invention.

DESCRIPTION OF THE INVENTION

Figure 1:
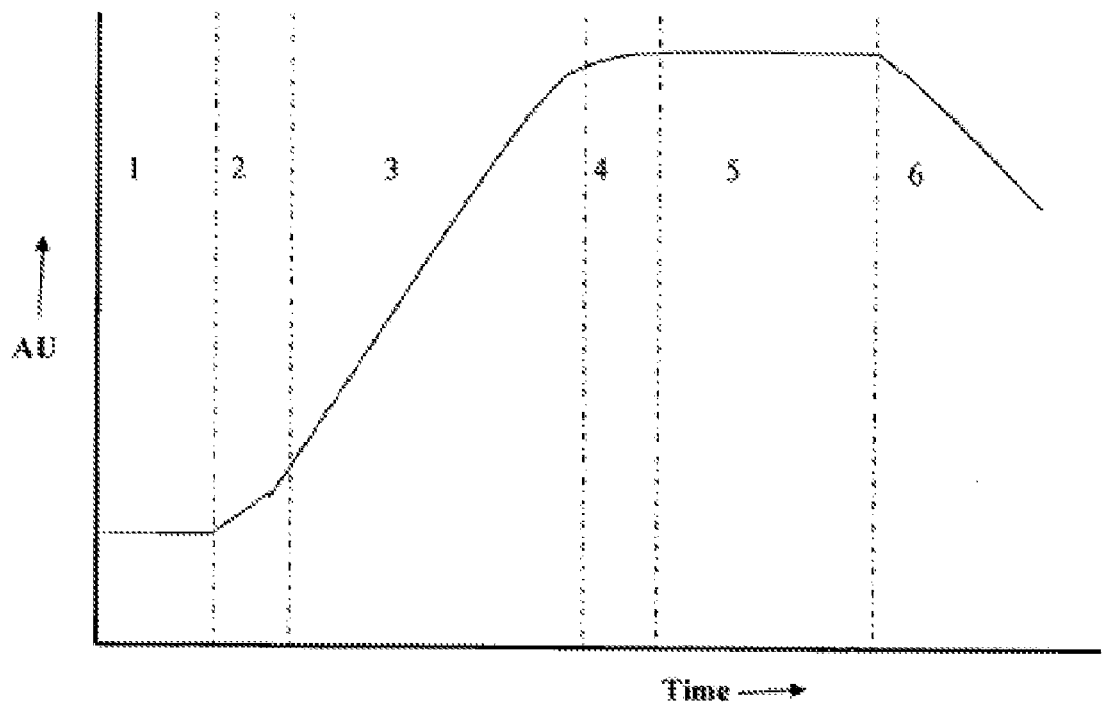
Figure 2:
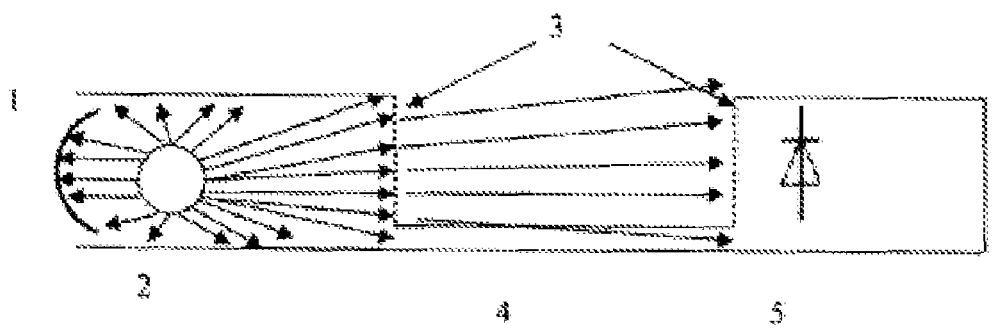
Figure 3:
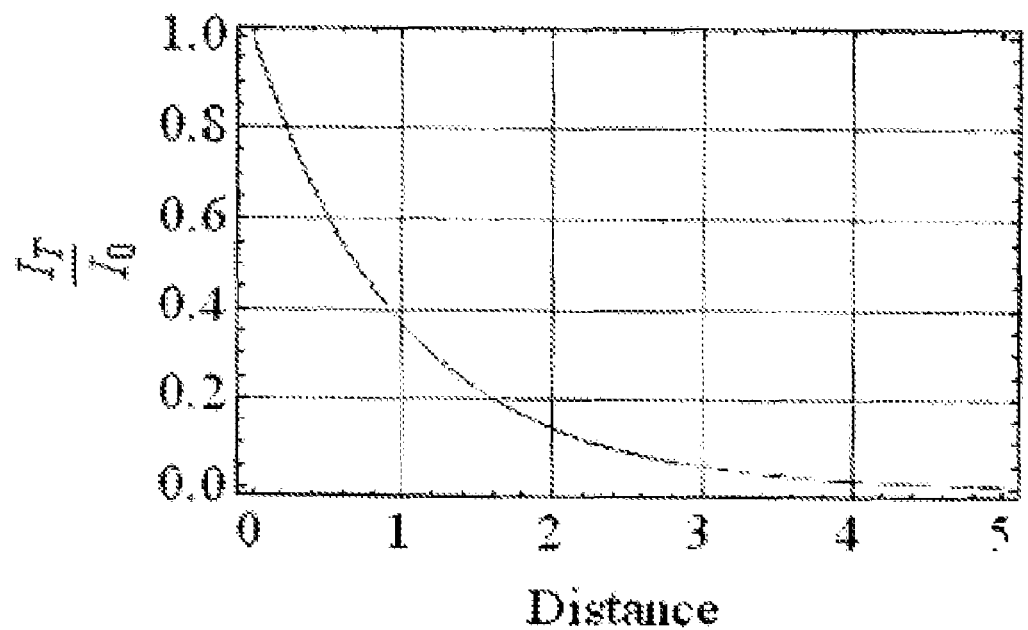
Figure 4:
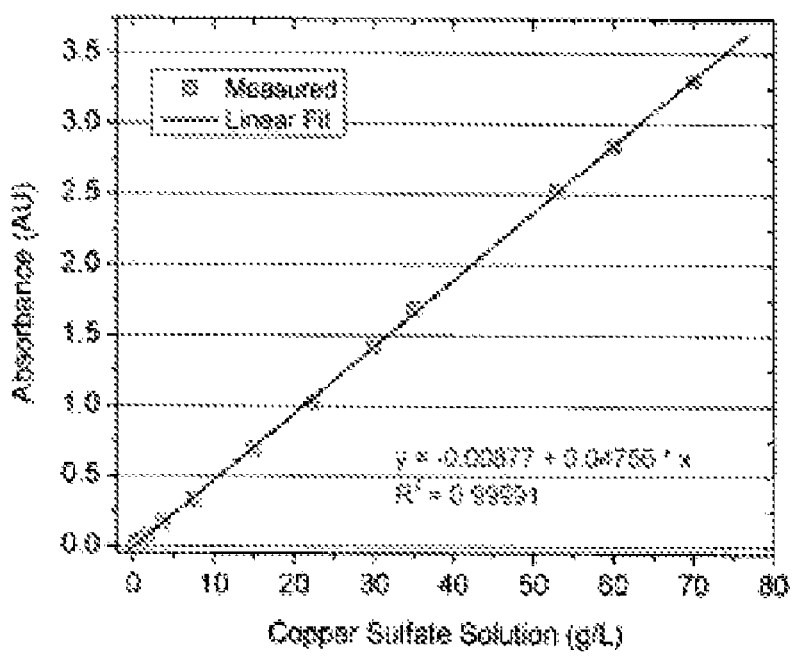
Figure 5:
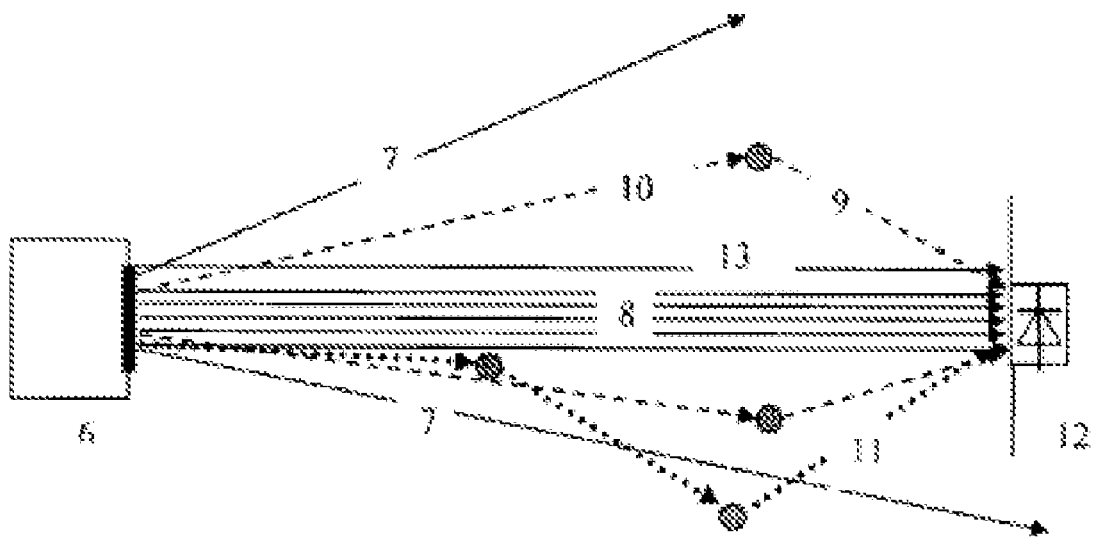
Figure 6:
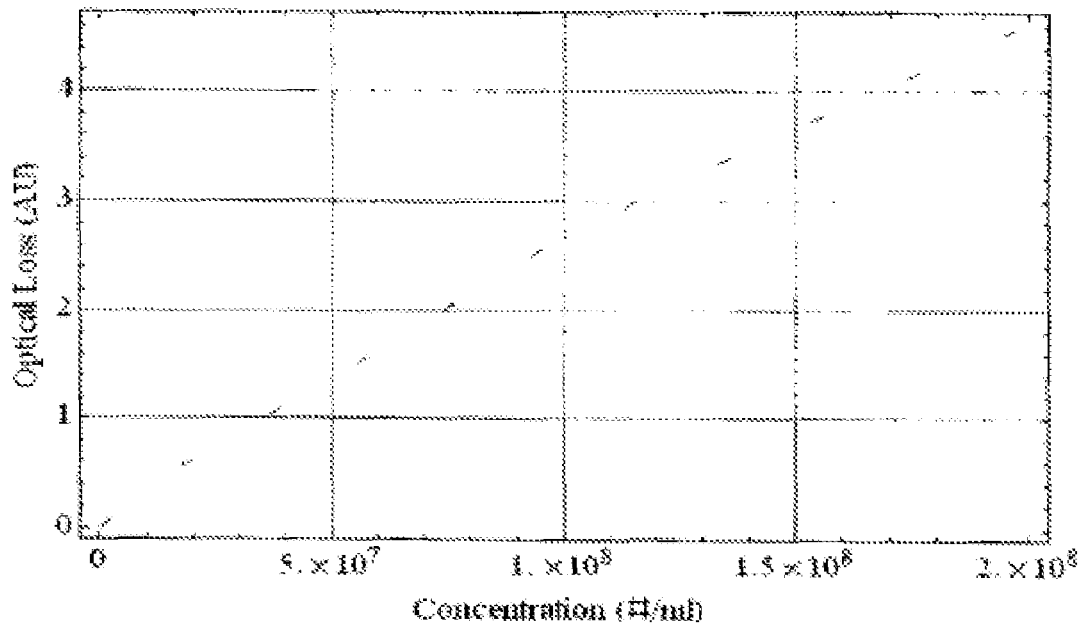
Figure 7:
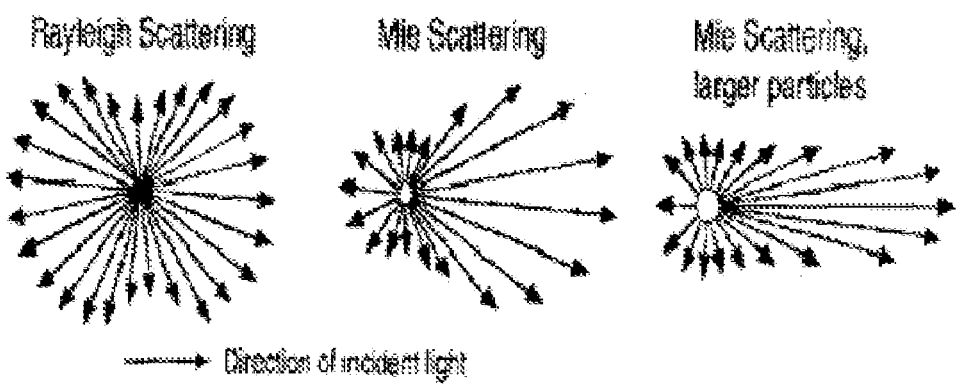

Turbidity meters, and many other optical systems (e.g.: spectrophotometers) which look at forward transmitted light (whether directly propagated and/or singly scattered) will manifest a deviation from Beer's Law (linear relationship between loss and scatterer concentration) caused by the light not taking a linear path into the detector. This is because many of the photons in the linear path are multiply scattered but still end up hitting the detector area and/or also because the optical beam is larger than the detector area, but photons outside the linear path are nonetheless scattered into the detector as is depicted in FIG. 5. Therefore, despite the increasing concentration of scatterers, the apparent loss seen by the detector does not significantly increase.

A more mathematical explanation of this phenomenon can be obtained through use of the Radiative Transfer Equation. This heuristic equation was introduced by Chandrakesar in 1950 [see Radiative Transfer (1950, Clarendon Press, Oxford; reprinted by Dover Publications, Inc., 1960)] and was initially utilized to describe the transfer of radiation through interstellar space. It has also found use in describing the transfer of radiation in atmospheric and oceanic environments. A version of the Radiative Transfer Equation is expressed below:

$$\left(\frac{1}{c}\frac{\partial}{\partial t} + \hat{n}\cdot\nabla\right)L(r) = -\xi L(r) + \frac{s}{4\pi}\int L(r)\beta(\theta,\phi)d\Omega \qquad \text{Eq. 4}$$

In Equation 4, L(r) is radiance at a single wavelength (monochromatic radiation) at position r, n is a unit vector in the direction of the scattered ray, c is the speed of light in the medium, $d\Omega$ is the solid angle integration differential (shown graphically in FIG. 8), θ and φ are the spherical coordinate system radial and azimuthal angles $\beta(\theta, \phi)$ while $d\Omega$ represents the probability that an incoming photon is scattered into the solid angle $d\Omega$, and $\xi$ is the sum of the absorption (a) and scattering (s) coefficients in units of inverse length.

The left side of Equation 4 describes the propagation of the light, with the first term in parenthesis giving the time dependence and the second giving the spatial dependence. The first term on the right of the equals sign describes the scattering and absorptive losses. The second term on the right describes the fraction of the total scattered light that can be collected by the detector The detector has a limited aperture and acceptance angle, and these factors limit the amount of the propagating and scattered light that will actually be recorded by the detector. Under steady state conditions $$\left(\frac{1}{c}\frac{\partial}{\partial t}L(r) = 0\right)$$

and when scattering is negligible (s~0), so that Equation 4 reduces in one dimension to:

$$L(x)/L(0) = e^{-\xi x} \qquad \text{Eq. 5}$$

This is Beer's law as shown in Equation 1 but expressed using radiance, L(r), instead of intensity, I. Thus it is seen that within certain limits the Radiative Transfer Equation can be reduced to Beer's law. If one limits the solid angle in the integral in Equation 3, thereby reducing the integral itself, one can also achieve the same steady state approximation to the Radiative Transfer Equation. Specifically, if the detector's field of view, as defined by the angles θ and φ, is very small then the integral is close to zero and Equation 4 is reduced to Beer's Law.

The next question to be considered is the relationship between the solid angle of the detector and adherence to Beer's law. To what extent is it necessary to limit the detectors solid angle field of view in order to have the Radiative Transfer Equation reduce to Beer's law? As the density of scatterers increases, the approximation will tend to break down, but a starting approximation is needed. This question has been considered for aerosols [see N. L. Swanson, et al, *Limits of optical transmission measurements with application to particle sizing techniques*, Applied Optics Vol. 38, No 27, p. 5887, 1999; and U.S. Pat. No. 6,219,138] and mathematically described using definitions from scattering theory. This question has also been considered indirectly when measuring the extinction (the total flux scattered and absorbed by a particle divided by the flux geometrically incident on the particle). [see H. E. Rose, J. Appl. Chem., 2, 80, p. 217. 1952) and J. R. Hodkinson, Aerosol Science, C. N. Davies, ed. Academic Press NY 1966]. In this instance, it was concluded that the efficacy of the extinction measurement was also aided by limiting the angular acceptance of the detector.

By limiting the acceptance angle of the detector based on the forward scattering of the particles, modeled by Fraunhofer diffraction, it is possible to achieve extinction measurements with acceptable fidelity. Applying this method to the problem at hand, and assuming a spherical scatterer of diameter d, then the Fraunhofer pattern from the projected disk of diameter d determines a Bessel function diffraction pattern. Further, if the angular acceptance of the detection aperture is limited to about one tenth of the angular spread of the first lobe of the Bessel function, a sufficiently small amount of the forward scattered light impinges on the detector.

This forward scattering limitation can then be expressed in radians as the following acceptance half angle:

$$\theta_{1/2} \leq 0.383 \frac{\lambda}{\pi d} \quad \text{Eq. 6}$$

This can be expressed in degrees as:

$$\theta_{1/2} \leq 7\frac{\lambda}{d} \quad \text{Eq. 7}$$

In Equation 7, d is the assumed diameter of the scatterer and $\lambda$ is the wavelength of the illumination source. Using Equation 7, I have found it is possible to determine the aperture sizes required to have the integral in Equation 4 be small enough to be negligible under the assumed conditions. That is, for a given assumed particle size and wavelength one can determine the solid angle of integration which is small enough so that Equation 4 reduces to Beer's law. This solid angle determination can be reduced to a two dimensional problem and a detector aperturing requirement. In the present invention, I apply this mathematical analysis to biological scattering and the measurement of cell density.

Typical mammalian cells (e.g.: CHO, or Chinese Hamster Ovary) are on the order of 10 microns in diameter, while many microbes (e.g.: E-Coli) are on the order of 2 microns in diameter. Recent studies [see Drezek et al., *Applied Opt.* 38:16, 3651-3661 (1999)] have shown that the majority of the scattering results from the higher index of refraction organelles situated within mammalian cells. Additionally, it is known that the diameter of these organelles is much smaller than the diameter of the cells themselves. The exact index of refraction of the organelles is not always precisely determinable. However, this parameter along with the size will determine their scattering function. Using the published data mentioned above, I have found that one can approximate the scattering behavior of many mammalian cell organelles using 2 micron polystyrene spheres.

This criterion is utilized below in order to determine what limiting angle is required for Beer's law to hold. Using Equation 7 and assuming a wavelength of 830 nm (0.83 microns) and 2 microns as the diameter of the scatterer, we have $$\theta_{1/2} \leq 7°\frac{\lambda}{d} = 7\frac{0.83}{2} = 2.905° \quad \text{Eq. 8}$$

This means that the 2D acceptance half-angle (2D projection of the solid angle) should not exceed 2.905° in order to have Beer's law hold to the maximum extent possible, again assuming that the solution contained only 2 micron diameter scatterers. If the solution contained scatterers up to 10 microns, then the acceptance half angle would need to be 5 times smaller in order to similarly limit the angular detection. As the scattering density increases, the system will reach a point where the amplitude of the forward scattered light will be within an order of magnitude of the light that is otherwise reaching the detector. It is at this point that the system will begin to deviate from Beer's law.

Figure 8:
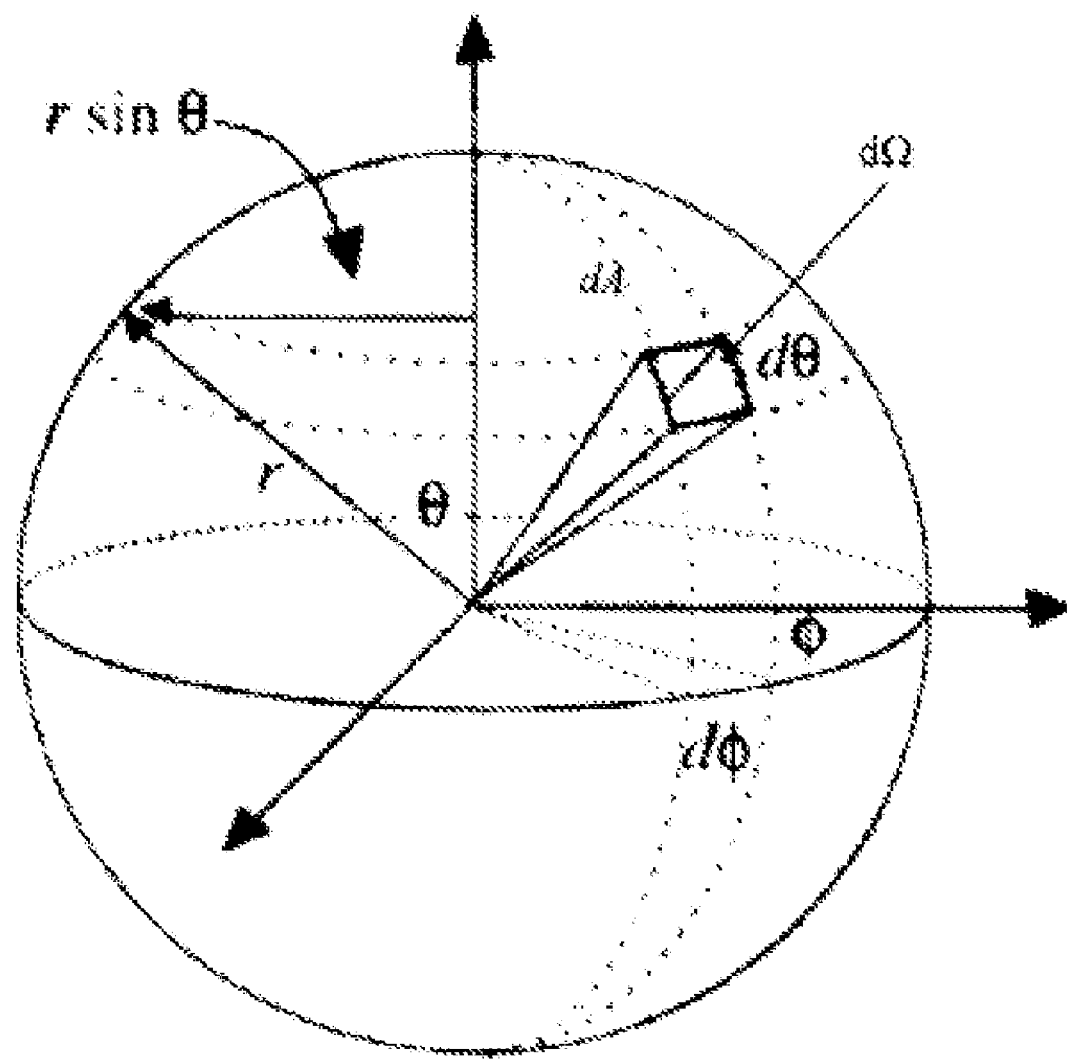
Figure 9:
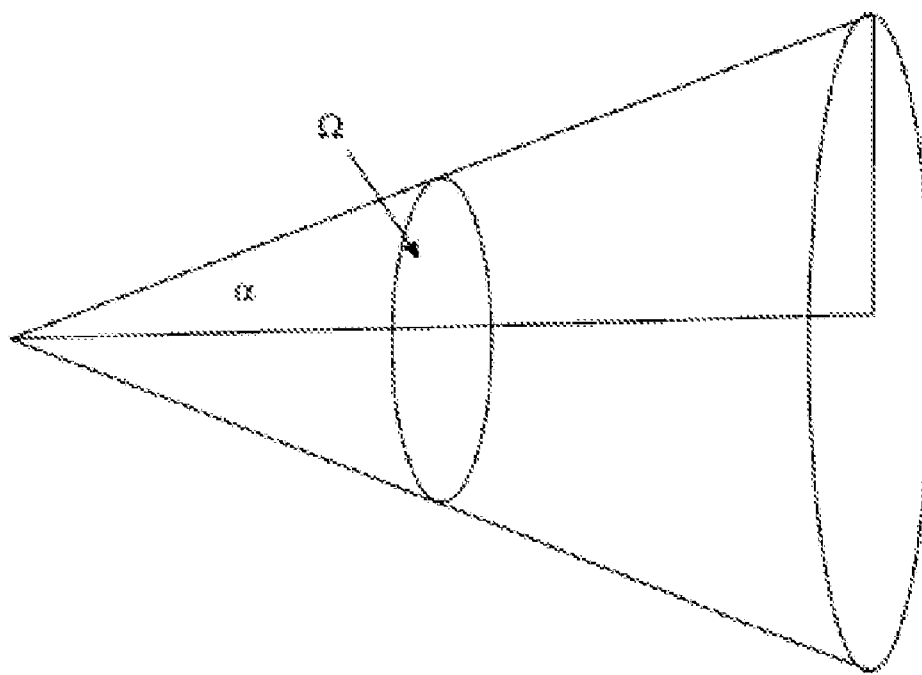

In order to construct a linear cell density probe using Equations 6, 7 and 8, this 2D angle, $\theta_{1/2}$, must be used to understand the 3D solid angle, $\Omega$, from which a cell density probe would gather light [see for example: R. McCluney, *Introduction to Radiometry and Photometry*, Artech House, 1994]. A diagrammatic description of the solid angle is show in FIG. 8, which depicts the projected area on the surface of a unit sphere. FIG. 8 shows a geometry used to calculate the solid angle, $\Omega$, subtended when specified by a 2-D plane angle $\alpha$. Following the teaching of McCluney one finds that the solid angle can be defined as:

$$\text{Solid Angle} \equiv \Omega = \frac{A}{R^2} = 2\pi[1 - \cos(\alpha)] \quad \text{Eq. 9}$$

Figure 10:
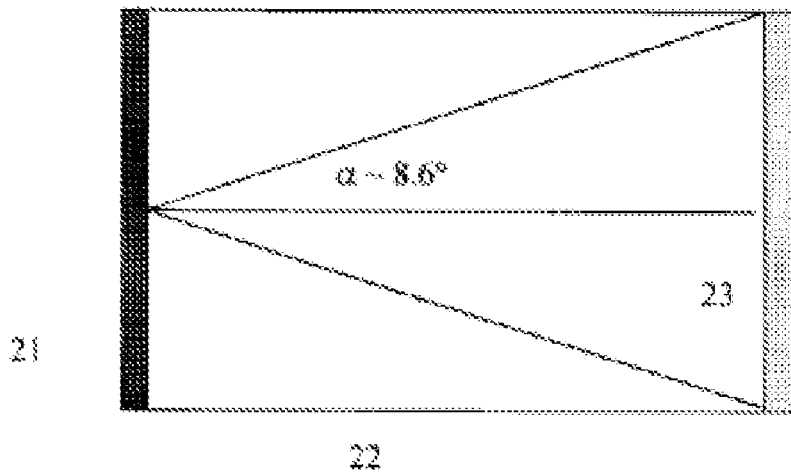

Applying Equation 9 to a probe geometry shown in FIG. 10, one can estimate the minimum solid angle from which its detector collects light. Note that a typical prior art cell density probe/turbidity meter is designed without concern for the solid angle from which the detector collects. A typical forward scattering cell density probe has a detector that is on the order of 5 mm in diameter with no intentional solid angle limiting aperture, and the light source is often even larger in cross-sectional area than the detector face. The fact that the optical beam is larger in cross-sectional area than the detector's active area means that with a low density of scatterers light which is not linearly directed at the detector's active area is simply not seen by the detector, while as the density of scatterers increases it is likely that even this light will be scattered into the detector. The consequence of this behavior is that the probe will exhibit an earlier onset of a non-linear response.

In FIG. 10, 21 is the scattering source, 22 is the gap, and 23 is a point on the detector surface used to approximate the solid angle viewed by the detector. Assume the length of gap 22 is 10 mm, and the light emitting aperture is 4 mm and further assume that the source is immediately scattered and can be thought of as a 4 mm diameter disc at the face of the optical source. This is a best case scenario and will underestimate the solid angle from which the detector will collect. In reality, the scattering will occur over the entire path from emitter to detector when scatterers are present. Using the geometry discussed above and shown in FIG. 10, we know that $\alpha \sim 8.6°$.

Using Equation 9 it is possible to calculate the projected solid angle for a symmetrical system as follows:

$$\Omega_{st}=2\pi[1-\cos(8.6)]=0.07 \text{ steradians} \qquad \text{Eq. 10}$$

This is equal to approximately $\pi/50$ steradians. In reality, since the scattering in the media occurs all the way from the source to the detector the scattering source is actually distributed along and around the gap between the detector and the source. Accurate calculations of the true source from which the detector collects would entail a Monte Carlo simulation of the scattering along this path. The real source will therefore be larger than a simple disk at the exit face of the illumination system and will be a three dimensional source. Additionally, the precise solid angle of collection depends on the exact geometry, sizes of the detector and light source, and the relationship between the wavelength of light and the scatterer size. There is the potential for optical radiation to scatter into the detector from almost all directions and from all locations in the gap between the detector and the light source. This would lead to a worst case where $\alpha$ can approach $\pi/2$, which would lead to a solid angle of $2\pi$ steradians, or collection from the entire half sphere of radius R. While it is unlikely that the detector would see radiation emitted from exactly half a sphere, to a first order it is likely to see a somewhat larger fraction of it than the first order approximation, as shown in Equation 10. Despite the fact that the solid angle viewed by the detector in the prior art probes is generally closer to $2\pi$ than to the number represented by Equation 9, we now can use this result as an upper limit to understand the effect of apertures to limit the solid angle.

Using the results of Equations 8 to limit the solid angle aperture such that the useable linear response range is maximized, the limits of the integral in Equation 8 are greatly reduced. The resulting solid angle is calculated below:

$$\Omega_{apertured}=2\pi[1-\cos(2.9)]=0.008 \text{ steradians} \qquad \text{Eq. 11}$$

$$\Omega_{apertured} \approx \pi/400 \text{ steradians}$$

Taking the ratio of the solid angles $\Omega_{apertured}/\Omega_{standard}$ and multiplying by 100 in Equation 12 below we can estimate a percentage of solid angle that the apertured system of the present invention subtends compared to existing systems:

$$\% = \frac{\Omega_{apertured}}{\Omega_{st}}100 \approx 6\% \qquad \text{Eq. 12}$$

Given that we have assumed a best case for the limiting aperture of a typical prior art cell density probe, it is clear that the level of aperturing and solid angle limiting instructed by Equation 8 would not be achievable without intentional design based on the above analysis.

Figure 11:
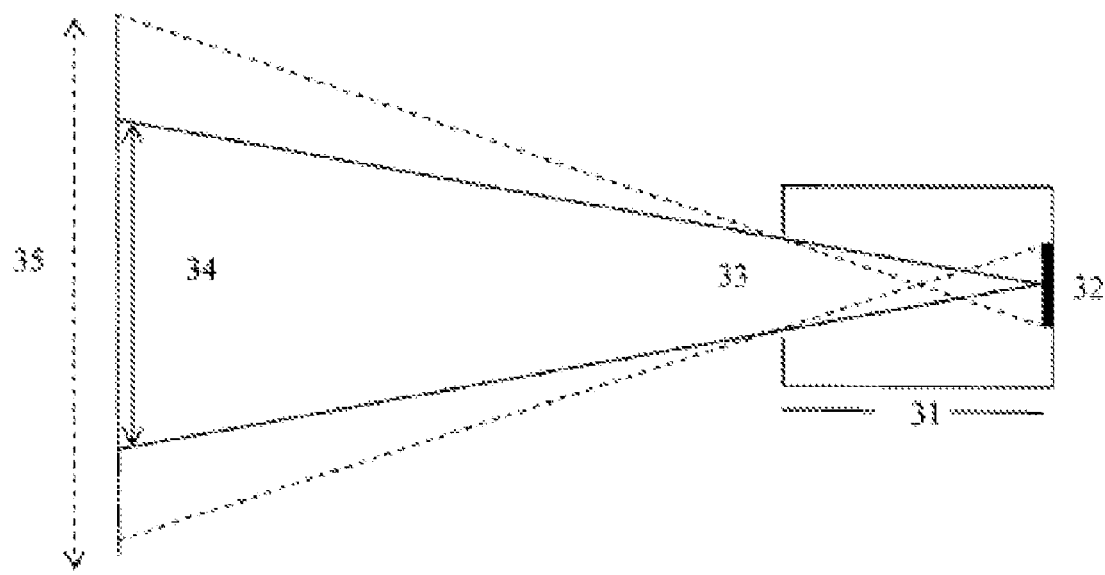

It should also be noted that according to McCluney (see R. McCluney, *Introduction to Radiometry and Photometry*, Artech House 1994), when two apertures are used, or when the detector has a finite area, it is possible to define the detector's field of view (solid angle) in more than one way. This scenario is depicted in FIG. 11, where 31 is the distance between the first and second aperture, or equivalently the distance between the first aperture 33 and detector 32 where the detector's foot print determines its spatial extent. 34 is the apparent area, $A_f$, seen by the center of the detector, 35 is the apparent area, $A_f'$, seen by the entire detector. FIG. 11 shows that it is possible to define an area associated with the field of view or solid angle $A_f$. It is also possible to define the area seen by the whole detector, $A_f'$ which is larger than the area, $A_f$, seen by the center of the detector. The smaller area is used for calibration purposes, and the larger area is used for calculating what is actually seen by the detector.

As mentioned previously, a probe designed in accordance with my invention limits the solid angle from which the detector collects light. This is often referred to as aperturing. By this, I mean the process where one uses one or more apertures, or alternatively a cylindrical tube in front of the detector to limit the solid angle of light that can impinge upon the detector. Although an example of this type of design will be discussed shortly, it should be noted that it is counterintuitive to aperture the detector in a system where light gathering is critical. However, I have found that a preferred way of overcoming the issue of low light levels received by the detector is by using phase sensitive detection methods (e.g., a lockin amplifier). This is especially advantageous where the signal to noise ratio is low due to the light limiting nature of the aperturing. As mentioned previously, in order to maintain the integrity of the signal at low levels the system must be designed accordingly. The illumination beam will preferably be a spatially coherent light source that is collimated. This allows one to have an illumination beam that is matched to the aperture size. Specifically, if the beam is substantially Gaussian or super-Gaussian, it is possible to simultaneously use a relatively low power optical source and still have the bulk of the power reach the detector even when there is a low concentration of scatterers present. For instance, if the Gaussian beam diameter is significantly smaller than that of the aperture (aperture radius >2.3 times the beam radius) there is essentially no power loss. If the Gaussian beam diameter is substantially larger than the aperture (as is frequently preferred to avoid alignment issues), the system is more immune to potential issues caused by physical misalignment between the optical source and detector during use. The most preferred situation from an aperturing perspective is a super-Gaussian or flat top beam distribution. This results in the optical power reaching the detector being unchanged irrespective of any pointing drift of the illumination source.

Particularly preferred embodiments of the present invention utilize a substantially monochromatic light source, especially a laser, and a silicon photodiode as a detector. Suitable lasers include edge emitting lasers, fiber coupled lasers, and vertical cavity surface emitting lasers. Particularly preferred lasers will be continuous wave, although pulsed lasers are also useable. To minimize the absorption of the light by the aqueous medium the light transmitted across the optical gap will preferably have a wavelength of from about 810 nm to 850 nm, most preferably ~830 nm, and the detector will preferably have a receiving aperture such that the solid angle of the light impinging on the detector will be less than $\pi/50$ radians.

For my experiments, a continuous wave (CW) laser source at ~830 nm is modulated at ~1500 Hz, and the signal from the photodiode detected using a lock-in amplifier. Note that although the exact modulation frequency is not of major significance, it should preferably be fast enough to avoid the 60 Hz modulation of room lights, be out of the 1/f noise range, and be slow enough that the optical source being modulated can respond. An additional consideration is that as the modulation frequency increases, generally so also does the instrument cost. A preferred range of modulation frequencies is therefore 200 Hz$\leq$f$\leq$20 KHz. Phase sensitive detection methods are preferred since they help with both noise rejection and signal integrity at low light levels. The above analysis has been tested using polystyrene micro-spheres which effectively simulate the scattering caused by the organelles present inside a mammalian cell.

Figure 12A:
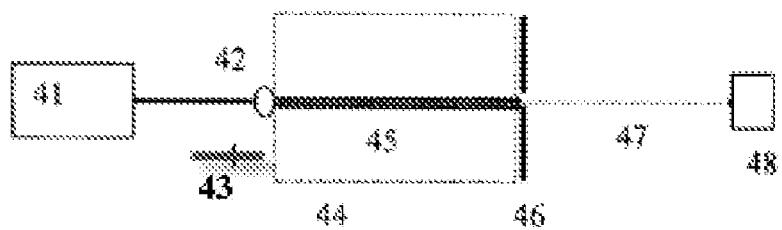
FIG. 12a is schematic representation of a cell density probe configured in accordance with the teaching of the present invention.
Figure 12B:
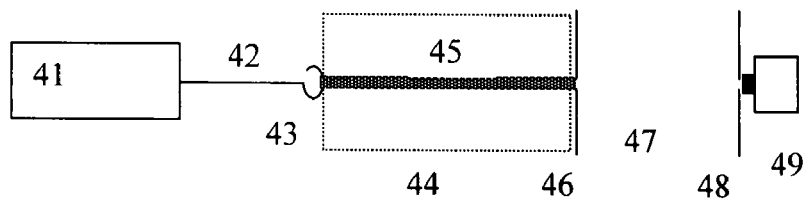
FIG. 12b is a probe design similar to that of FIG. 12a but which utilizes two apertures
Figure 12C:
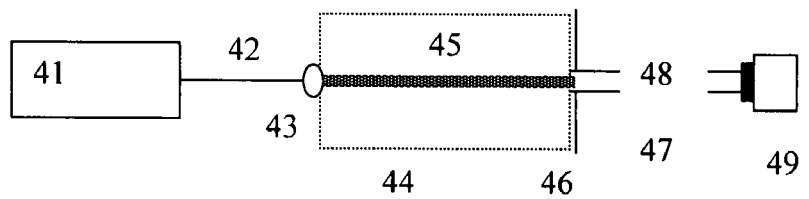
FIG. 12c is a probe design similar to that of FIG. 12a but which utilizes a cylindrical tube to perform the aperturing.
Figure 12:
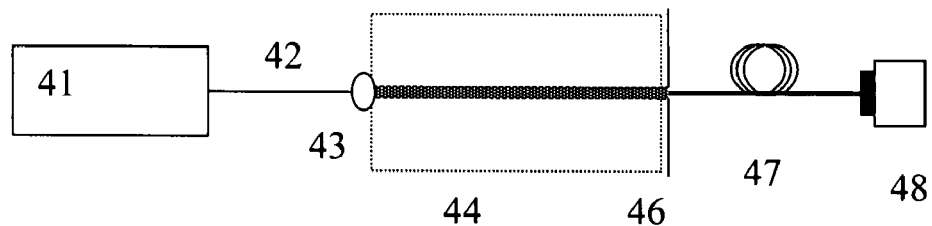

An assembly designed and constructed in accordance with the present invention is shown schematically in the FIG. 12a in which the numbered components are as follows:

41. A ~830 nm semiconductor CW laser source
42. The optical beam
43. A collimating lens
44. The optical gap
45. The optical beam traversing the gap
46. Aperture 1
47. The distance between the first aperture and the detector
48. The detector, where the physical size of the detector acts as an aperture The optical distance between the fiber-coupled, collimated ~830 nm laser source and the first aperture is 10 mm (i.e., the optical gap distance), while the distance (47) between the first aperture and the detector is approximately 20 mm. The diameter of the aperture (46) is 400 microns and of the detector (48) itself is approximately 500 microns. The acceptance half-angle is approximately 0.50, and with the illumination wavelength of ~830 nm, and the scatterer diameter of 2 microns, Equation 8 indicates the solid angle has been limited sufficiently to ensure linearity The aperture sizes are calculated to give the solid angle desired based on the teaching of Equation 6, which provides the angle in one dimension to which the detector's field of view must be limited for a given wavelength of the illuminating source and a given expected diameter of the scatterer. This was converted into a two dimensional symmetrical solid angle in steradians, and the size of the apertures selected. In order to limit the solid angle at least two apertures (or the equivalent thereof) are required. These two apertures can effectively be created by using a single aperture which is separated by a distance from a detector which is limited in cross-sectional area as shown in FIG. 12a, or alternatively, it can be two individual apertures separated by a distance, or a cylindrical tube where the inner diameter acts as the aperture size, and increasing the tube length restricts the solid angle. These second and third alternative embodiments are depicted schematically in FIG. 12b and FIG. 12c respectively. Note that in FIG. 12b the numbered components are as follows:

41-47 same as in FIG. 12a
48. The second aperture
49. The photo-detector which is larger in diameter than the second aperture In FIG. 12c the numbered components are as follows:

41-47 same as in FIG. 12a
48. A cylindrical tube which acts as two apertures separated by a distance (47)
49. The photo-detector which is larger than the inner diameter of 48.

FIG. 12d shows a similar system where the solid aperture is created by use of an optical fiber instead of discrete apertures. In FIG. 12d the numbered components are as follows: 41-46 same as in FIG. 12a,
47. An optical fiber with defines a specific numerical aperture
48. The photo-detector Often, the same solid angle can be achieved with different combinations of aperture size and distance. It is often advantageous to have a compact system and in this case, smaller apertures are preferably utilized. However, from a functionality perspective larger aperture diameters and a larger distance can be used to achieve the same limiting solid angle.

Figure 13:
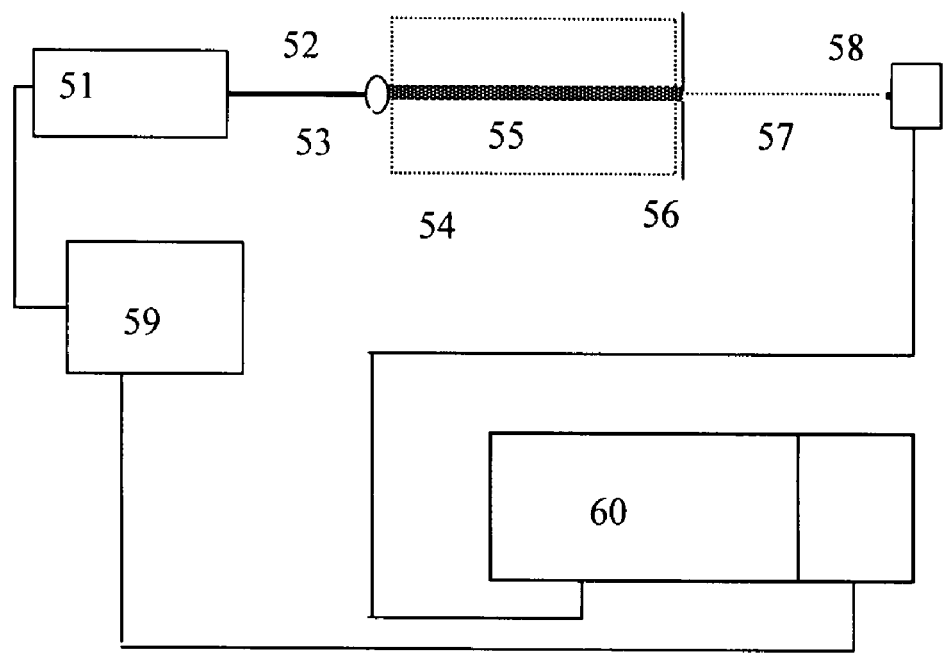
Figure 14A:
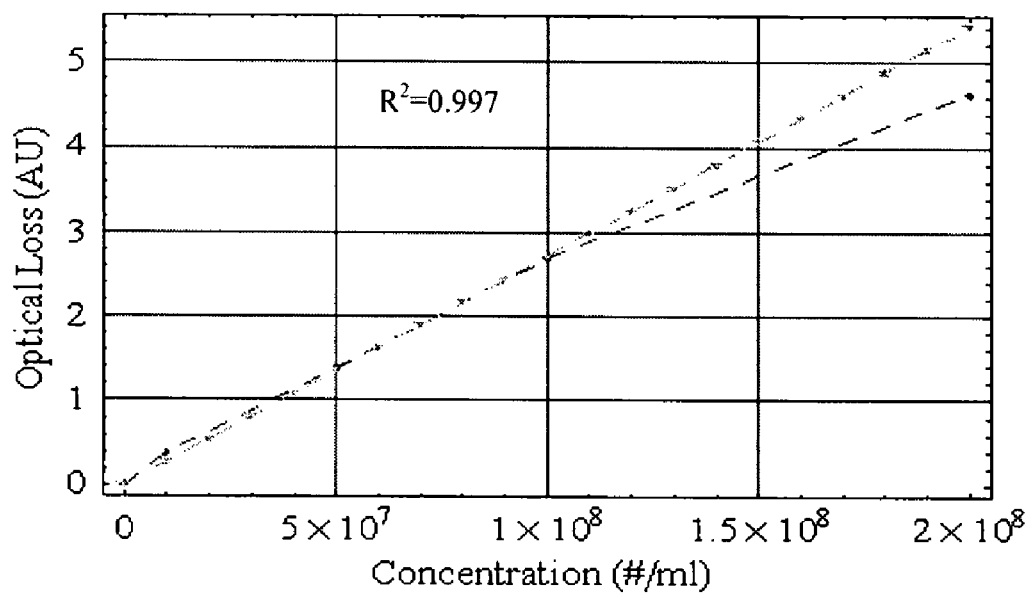
Figure 14B:
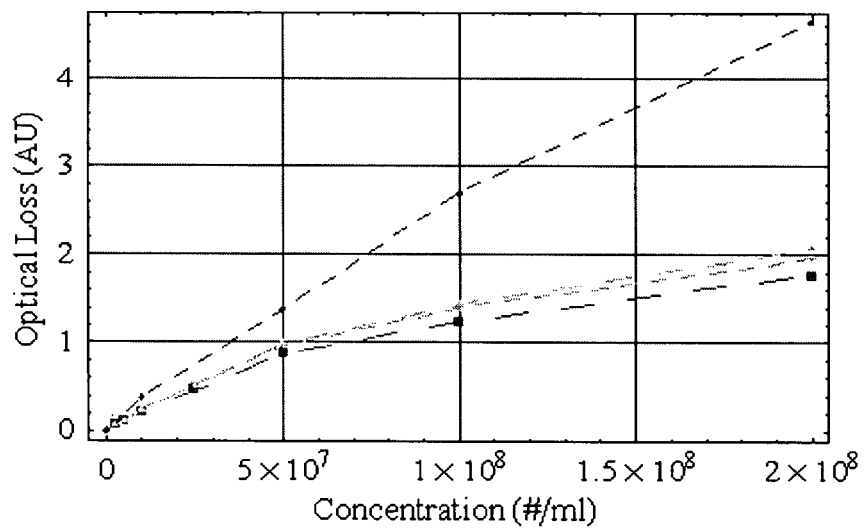

A block diagram of a preferred embodiment of a system in accordance with the present invention is shown in FIG. 13 with the numbered components as follows:

51-58 same as in FIG. 12a
59. Laser diode current driver and TE cooler controller
60. Lockin amplifier and modulation source This system was tested with different concentrations of ~2 micron scatterers. The scatterers used were polystyrene microspheres which were chosen because they are available with a known mean diameter, concentration, and index of refraction. The results of the scattering tests are shown in FIGS. 14a and 14b. In FIG. 14a, the dashed line is the actual data, and the dotted line is a least squares fit to the first 4 of 5 data points. The quality of the fit, as indicated by the $R^2$, is very good. The function starts to deviate from a straight line above about 3 AU, or above a concentration of $10^8$ scatterers per ml. Interpretation of the results above a concentration of $10^8$ scatterers per ml is somewhat difficult, as the sampling density is not high enough to reveal exactly where deviation from a linear response begins. Nonetheless, this design shows an increase >2 AU (i.e., >2 orders of magnitude) in the range of linearity as compared to prior art systems.

Additionally, as shown in FIG. 14b, the dynamic range of the probe is extended by more than 2.5 AU, i.e., a probe in accordance with the present invention provides suitable measurement accuracy for most aqueous solutions over the range of from 0 (distilled water as a base line) up to about 4 AU. In many fermentation applications, the small dynamic range of available probes significantly limits their usefulness. For example, if the density of the batch starts at around 0.5 to 1.5 AU and ends around 3.5 AU, prior art probe systems do not have a response that allows for continuous and accurate monitoring of the process.

A cell density probe in accordance with the present invention can also be used with disposable bioreactor technology. It can be used in both disposable polymeric bag bioreactors and other types of disposable bioreactors so that the probe can be placed in a preferred location within the disposable bioreactor. Preferred here means where the mixing is continuous and the fluid present is representative of the contents of the bioreactor. Additional considerations include the possibility of allowing the more expensive optical components (e.g., the light source and the detector) to be physically separated from the components which define the optical gap so that the system is economically viable.

Figure 16:
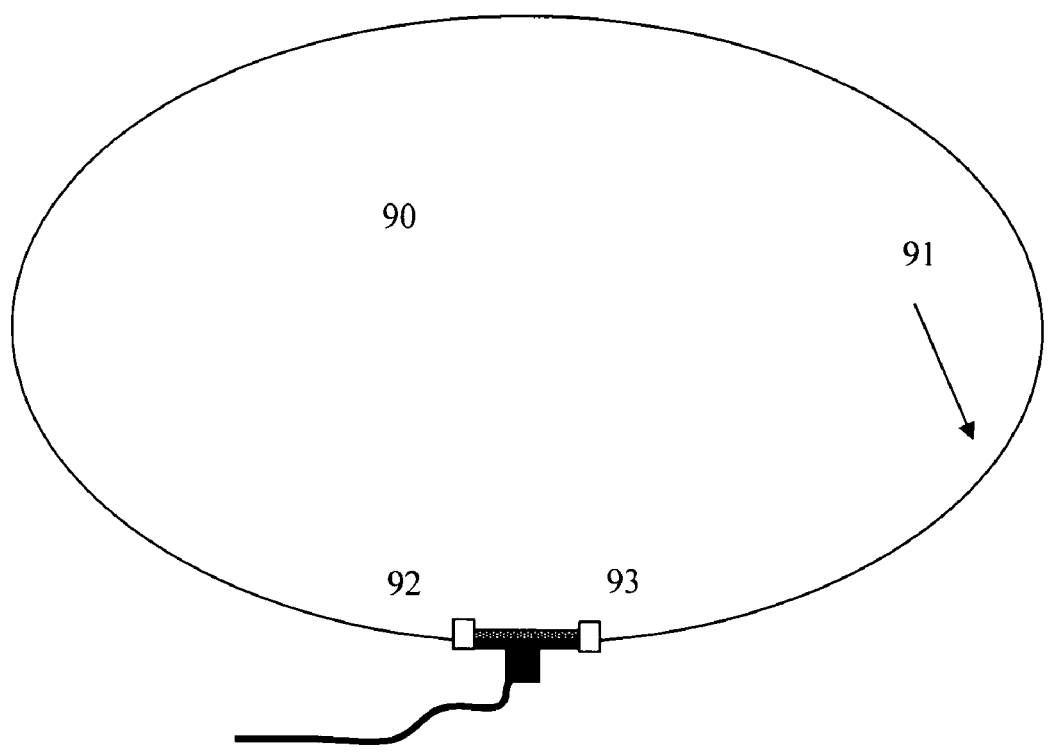
Figure 17:
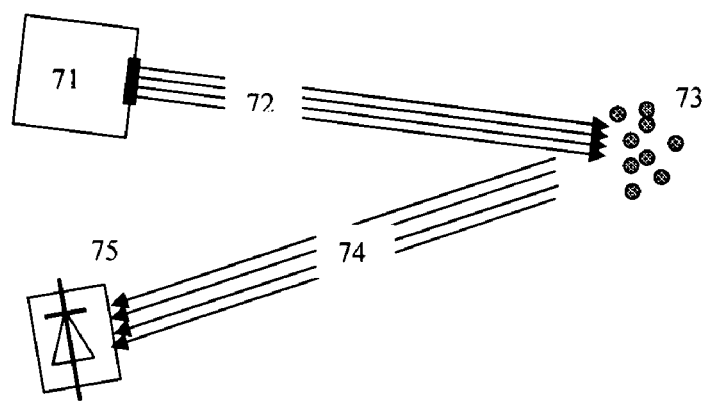

In FIG. 16, a disposable bag bioreactor, 90, is shown from a top view with the disposable cell density probe attached through the side wall, 91, of the disposable bioreactor. 92 is the optical source and 93 is the detector apertured according to my previous teachings. In this embodiment the optical gap is defined by a sample cell which interfaces to the bioprocess and which is physically separable from the optical source and detector. In this embodiment the source and/or detector will preferably be inexpensive and hence disposable. Additionally, the source can be fiber coupled to the emitting aperture, and an optical fiber can be used as the light collecting aperture, while simultaneously limiting the numerical aperture.

Figure 15:
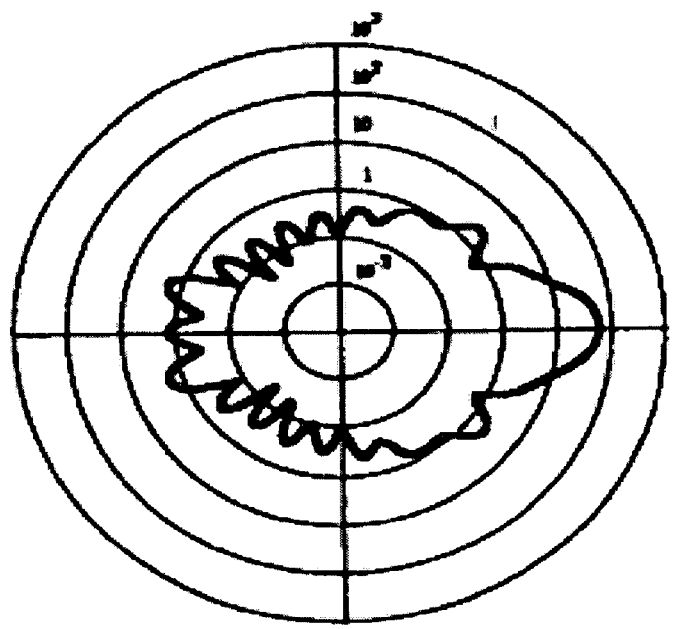

To this point, we have considered scattering issues primarily in terms of forward scattering and detection. It is important to note that the inventive concepts disclosed here can also be applied to the detection of backwards scattered optical radiation. Backscattering and the Radiative Transfer Equation have been studied for aerosols [see W. G. Tam, *Aerosol Backscattering*, Applied Optics, Vol. 22, No. 19, p. 2965, 1983 and A. Deepak, Atmospheric Radiative Transfer, 1993]. By analogy to the design for a forward scattering system, a backscattering system with a response that is linear with the concentration of the scatterers can be designed. As can be seen in FIG. 15 the backscatter in the Mie regime will generally be relatively small compared to the forward direction scatter. The case shown in FIG. 15 indicates what is to be anticipated for a mammalian cell with a diameter of ~8.5 microns and an illumination wavelength of 0.83 microns. FIG. 15 is a "phase' diagram giving the magnitude of the scattering as a function of direction, and is plotted on a logarithmic scale. One can see that the directly backscattered light is almost 100 times weaker than the forward scattered light.

A scattering probe that detects backscattered light works in essentially the opposite way from a forward scattering probe i.e., when the scattering density is high, there will generally be more light impinging on the detector and when the scattering density is low there will be a comparatively small amount of light incident upon the detector. However, since the specific advantage of the present invention is the construction of an optical scattering probe that has an inherently linear response to scattering density, either design is superior to the prior art.

Figure 18:
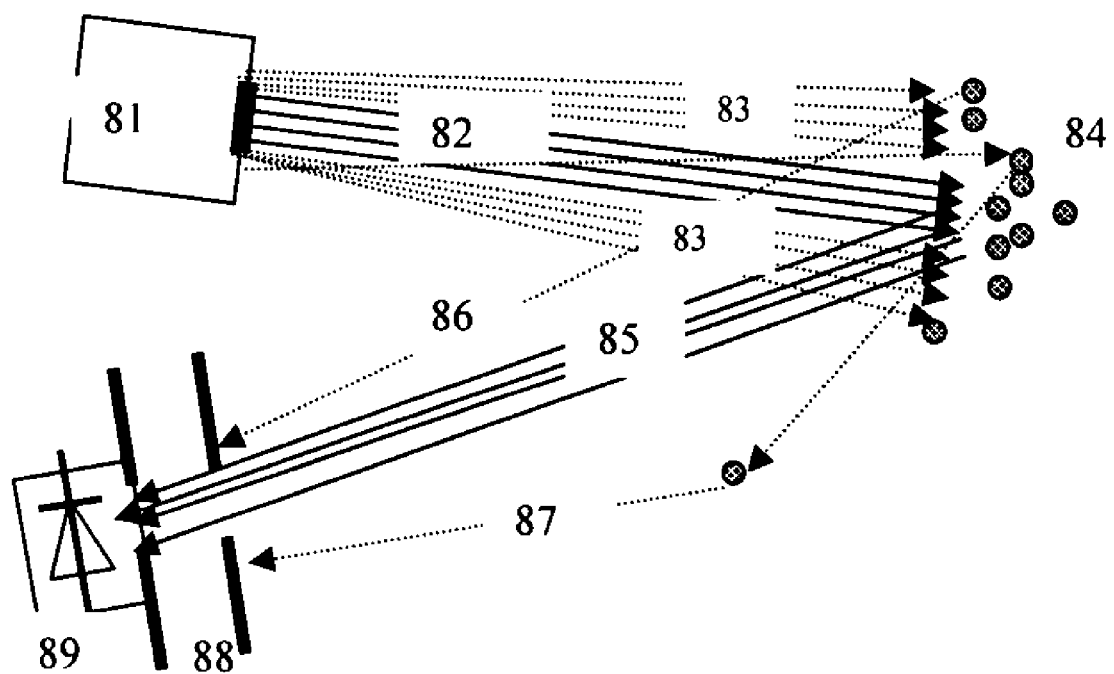

Considering the system shown in FIG. 18, one can see a preferred embodiment of the present invention in which the excitation source and the detector are offset in angle. This is to allow for the collection of light at an angle to the excitation light path (as opposed to directly back) and thereby access a larger scattering cross-section. At a low density of scatterers in the medium it is to be expected that only singly backscattered light will hit the detector and that this light will be scattered in a linear proportion to the number of scatterers. As the density of the scattering medium increases, the light that before would not hit the detector will now hit the detector because of both large angle single and also multiple scattering. This causes the relationship to be supra-linear. While this situation is not covered by Beer's law, I have found that the mechanism for producing a linear system is substantially the same. This type of backscattering collection can also be modeled by using the Radiative Transfer Equations (Equations 4). By aperturing the detector so as to limit the solid angle of the light that can hit the detector, one can maintain a linear relationship between backscattered light and scatterer concentration. An apertured, backscatter detection system in accordance with the present invention is depicted in FIG. 18 with the components numbered as follows:

81. Light source
82. Rays that can always scatter into the detector's acceptance angle and position
83. Rays that can scatter into the detector's acceptance angle w/apertures
84. Scattering particles
85. Rays (2) post scattering event.
86. Rays (3) post scattering event.
87. Rays that are prevented from entering the detector due to multiple scattering
88. Solid angle limiting apertures
89. Photo-detector

The invention claimed is:

1. An optical loss probe manifesting a substantially linear response in optical loss vs. concentration of scatterers in an aqueous medium, said probe comprising:
   i) a source of light having a wavelength between about 810 nm and 850 nm
   ii) an optical detector,
   iii) an optical gap between said light source and said optical detector, said optical detector having a receiving aperture configured such that the solid angle of acceptance of the light passing through said optical gap and impinging on said optical detector is less than $\pi/50$ radians.

2. An optical loss probe in accordance with claim 1 wherein said substantially linear response is in the range between about 0 AU and about 4.0 AU.

3. An optical loss probe in accordance with claim 1 wherein said light source is substantially monochromatic.

4. An optical loss probe in accordance with claim 3 wherein said light source is a laser.

5. An optical loss probe in accordance with claim 4 wherein said laser is a continuous wave laser.

6. An optical loss probe in accordance with claim 4 wherein said laser is a vertical cavity surface emitting laser, a fiber coupled laser or an edge emitting laser.

7. An optical loss probe in accordance with claim 4 wherein said laser is collimated such that the diameter of the laser beam is within a factor of 10 of the diameter of the receiving aperture.

8. An optical loss probe in accordance with claim 4 wherein said light is modulated at a frequency in the range of 200 Hz to 20 KHz.

9. An optical loss probe in accordance with claim 1 wherein said light source is substantially spatially coherent.

10. An optical loss probe in accordance with claim 1 wherein said light source emits a beam which is substantially Gaussian.

11. An optical loss probe in accordance with claim 10 wherein said aperture has a radius >2.3 times the radius of said beam.

12. An optical loss probe in accordance with claim 1 wherein said light source emits a beam which is substantially Super-Gaussian or Flat Top.

13. An optical loss probe in accordance with claim 12 wherein said aperture has a diameter <75% of the beam diameter.

14. An optical loss probe in accordance with claim 1 wherein said light has a wavelength of approximately 830 nm.

15. An optical loss probe in accordance with claim 1 wherein said detector comprises a lock in amplifier.

16. An optical loss probe in accordance with claim 1 wherein said detector comprises a photo-detector.

17. An optical loss probe in accordance with claim 16 wherein said detector comprises a photodiode.

18. An optical loss probe in accordance with claim 1 wherein said detector comprises a silicon or avalanche photodiode.

19. The optical loss probe of claim 1, wherein at least one of the light source and the detector are physically separable from the sample cell which defines the optical gap.

20. A method for determining the concentration of scatterers dispersed in an aqueous medium comprising directing a light beam having a wavelength between about 810 nm and 850 nm across an optical gap containing said dispersed scatterers onto an optical detector having a receiving aperture configured such that the solid angle of acceptance of the light passing through said optical gap and impinging on said optical detector is less than $\pi/50$ radians.

21. A method in accordance with claim 20 wherein said optical detector utilizes phase sensitive detection.

22. A method in accordance with claim 20 wherein said light beam has a wavelength of approximately 830 nm.

* * * * *